US010441168B2

(12) United States Patent
Nieuwenhuis et al.

(10) Patent No.: US 10,441,168 B2
(45) Date of Patent: Oct. 15, 2019

(54) COMPUTER-IMPLEMENTED METHOD FOR DETECTING A CORNEAL VERTEX (71) Applicants: Carl Zeiss Vision International GmbH, Aalen (DE); Carl Zeiss AG, Oberkochen (DE)

(72) Inventors: Claudia Nieuwenhuis, Essingen (DE); Oliver Schwarz, Ellwangen (DE); Michael Gamperling, Leipheim (DE)

(73) Assignees: Carl Zeiss Vision International GmbH, Aalen (DE); Carl Zeiss AG, Oberkochen (DE)

( * ) Notice: Subject to any disclaimer, the term of this patent is extended or adjusted under 35 U.S.C. 154(b) by 28 days.

(21) Appl. No.: 15/881,367

(22) Filed: Jan. 26, 2018

(65) Prior Publication Data

US 2018/0214022 A1 Aug. 2, 2018

(30) Foreign Application Priority Data

Jan. 27, 2017 (EP) .................................. 17 153 558

(51) Int. Cl.
*A61B 3/14* (2006.01)
*A61B 3/10* (2006.01)
*G02C 13/00* (2006.01)
*A61B 3/107* (2006.01)
*G01M 11/02* (2006.01)
*G02C 7/06* (2006.01)
*A61B 3/11* (2006.01)

(52) U.S. Cl.
CPC ................. *A61B 3/14* (2013.01); *A61B 3/10* (2013.01); *A61B 3/1005* (2013.01); *A61B 3/107* (2013.01); *G02C 13/003* (2013.01); *G02C 13/005* (2013.01); *A61B 3/111* (2013.01); *G01M 11/0207* (2013.01); *G02C 7/061* (2013.01); *G02C 2202/22* (2013.01)

(58) Field of Classification Search
CPC ........... A61B 3/152; A61B 3/14; A61B 3/102; A61B 3/12; A61B 3/0025
USPC .......................................... 359/208; 351/208
See application file for complete search history.

(56) References Cited

U.S. PATENT DOCUMENTS

| 5,573,006 A | 11/1996 | Shimotani et al. |
| 2003/0081173 A1* | 5/2003 | Dreher ................. G02C 13/005 351/204 |
| 2003/0123026 A1 | 7/2003 | Abitbol et al. |

(Continued)

FOREIGN PATENT DOCUMENTS

| JP | 2007206211 A | 8/2007 |
| JP | 5854861 B2 | 2/2016 |

OTHER PUBLICATIONS

Hartley et al.: "Multiple View Geometry in Computer Vision," 2nd edition, pp. 1 to 8, Cambridge University Press 2004.

(Continued)

*Primary Examiner* — Mohammad A Hasan
(74) *Attorney, Agent, or Firm* — Ewers & Hasselmann PLLC (57) ABSTRACT A computer-implemented method detects the position of a corneal vertex of an eye from a frontal image of a head and a lateral image of the head. The front and lateral images are calibrated to one another, and the position of the corneal vertex in space is determined from the frontal image and the lateral image with a geometric position determination.

29 Claims, 5 Drawing Sheets

(56) References Cited

U.S. PATENT DOCUMENTS

| | | | |
|---|---|---|---|
| 2007/0195266 A1* | 8/2007 | Kubitza | G02C 13/003 |
| | | | 351/204 |
| 2011/0007269 A1* | 1/2011 | Trumm | G02C 13/005 |
| | | | 351/204 |
| 2011/0234977 A1* | 9/2011 | Verdooner | A61B 3/102 |
| | | | 351/207 |
| 2012/0148159 A1 | 6/2012 | Kaneda et al. | |
| 2016/0379093 A1 | 12/2016 | Yoshioka et al. | |

OTHER PUBLICATIONS

Din En Iso 13666 (Ophthalmic optics—Spectacle lenses), dated Oct. 2013.
Extended European Search Report issued in EP 17 153 558.6, to which this application claims priority, dated Oct. 12, 2017.
Partial European Search Report issued in EP 18151589.1, which is a counterpart of this application, dated Jun. 25, 2018.

* cited by examiner

COMPUTER-IMPLEMENTED METHOD FOR DETECTING A CORNEAL VERTEX

CROSS-REFERENCE TO RELATED APPLICATIONS

This application claims priority to European patent application EP 17 153 558.6, filed Jan. 27, 2017, the entire content of which is incorporated herein by reference.

TECHNICAL FIELD

The disclosure relates to a computer-implemented method for detecting the position of a corneal vertex from a frontal and a lateral image of a head by calibrating the images to one another and determining the position of the corneal vertex in space by a geometric position determination.

BACKGROUND

The corneal vertices of a subject are important points when determining centration parameters for fitting spectacles. Centration parameters are used to correctly arrange or center spectacle lenses in a spectacle frame such that the spectacle lenses are arranged at the correct position relative to the eyes of the spectacles-wearing person. Here, these are in part anatomical parameters of the relevant person, such as, the interpupillary distance, in part purely frame-specific parameters, such as, the frame disk width or the frame disc height, and in part combinations of anatomical and frame-specific parameters, such as, the vertex distance and the fitting point height. An overview of conventional centration parameters is provided by DIN EN ISO 13666, dated October 2013.

An at least approximate determination of the position of the corneal vertex in space and, typically, of the position of both corneal vertices in space, may be used advantageously in a further evaluation for determining centration parameters, in particular, for determining the vertex distance. Previously, the corneal vertex positions were manually annotated in the frontal and lateral images. Here, a reflection-based or pupil-based annotation was favored, depending on the preference of the optician. In the case of the reflection-based annotation, a light reflection is produced on the pupil with the aid of an LED, the light reflection being easier to detect than the pupil center. However, many opticians continue to prefer the pupil-based annotation.

A method of the type set forth at the outset is known from US 2011/0007269 A1. In this method, just like in the methods known from US 2003/0123026 A1, JP 2007/206211 A and US 2007/195266 A1, use is made of stereo algorithms, which are based on finding correspondences in images. A precondition in each case is a large overlap of the images, and so the selection of camera arrangements is greatly restricted. Here, arranging the cameras with very different recording directions in space is not possible.

SUMMARY

It is an object of the disclosure to provide a method with which the position of a corneal vertex in space can be detected more easily.

Proceeding from US 2011/0007269 A1, an exemplary method disclosed herein solves the problem of simplifying the method known in advance by pre-processing data.

Proceeding from US 2011/0007269 A1, an exemplary method disclosed herein avoids carrying out a complicated stereoscopic method.

Proceeding from US 2011/0007269 A1, an exemplary method disclosed herein solves the problem of simplifying the method known in advance by pre-processing data.

Proceeding from US 2011/0007269 A1, an exemplary method disclosed herein solves the problem of facilitating a more precise determination of the corneal vertex.

The method according to the disclosure creates a precondition for calculating centration parameters, such as the interpupillary distance and the vertex distance, to be precise both in the case of a 'real' centration with a real spectacle frame and in the case of a virtual centration, wherein spectacles or a spectacle frame are virtually "put on" the image of the subject if the geometric data of the spectacles or spectacle frame are available. In the process, provision is typically made of calibrated images that were recorded at the same time. The calibration thereof includes the extrinsic properties of the cameras recording the images or the camera recording the images in succession, such as the relative alignment of their optical axes and the relative alignment with respect to one another in space. Moreover, the calibration includes the intrinsic properties, i.e., the properties of the cameras themselves, which define how a point in space, which is situated in the internal coordinate system of the respective camera, is mapped onto the coordinates of the pixels of the recorded image. A detailed description of the calibration of cameras is found in the textbook entitled "Multiple View Geometry in Computer Vision" by Richard Hartley and Andrew Zisserman, 2nd edition, Cambridge University Press 2004, and, in particular, on page 8 therein. There, the use of a triangulation method is preferred within the scope of the geometric position determination of the corneal vertex in space.

The position of the corneal vertex in space, determined to a first approximation, is then subjected to a correction calculation. The type of correction calculation then depends on the way in which the position of the corneal vertex in space is determined to the first approximation.

According to a first exemplary embodiment of the disclosure, provision is made within the scope of a so-called pupil-based evaluation for the position of the corneal vertex in space to be determined to a first approximation as a point of intersection of a view ray, tangential to the cornea, from a lateral camera recording the lateral image with a view ray, directed onto the pupil, from a frontal camera recording the frontal image. If this is the case, the position of the corneal vertex is typically calculated according to $a = q + \mu^* v + \mu^* w$ with the correction calculation, where a denotes the position vector of the corneal vertex in space after carrying out the correction calculation, q denotes the position of the corneal vertex to a first approximation, µ denotes an empirical value or an actual value for the distance between the pupil center and the corneal vertex, v denotes a unit vector in the spatial direction from the pupil center to the frontal camera and w denotes a unit vector in the viewing direction extending through the center of a corneal sphere.

According to a second exemplary embodiment of the disclosure, provision is made of undertaking a reflection-based evaluation by virtue of a flash being produced, preferably by means of an LED, when recording the images, wherein the position of the corneal vertex in space is determined to a first approximation as the position of the reflection point of the flash on the cornea. Proceeding from this first approximation, the position of the corneal vertex in the horizontal direction proceeding from the reflection point is approximately corrected by means of the correction calculation by adding $\Delta x = +/- r^* \sin(\frac{1}{2}^*(\arccos z/a + \arctan x/(z-v)))$ to the x-coordinate when the flash is produced with a light source arranged centrally in front of the face of the subject. In the correction calculation, r denotes an empirical value or an actual value for the corneal radius, a denotes the distance between the optical center of a frontal camera recording the frontal image and the reflection point, x and z denote the x- and z-coordinates of the reflection point in a coordinate system with the origin at the optical center of the frontal camera, wherein the viewing direction of the frontal camera corresponds to the z-direction and the x-direction is horizontally orthogonal to the z-direction and, when observed in the z-direction, points to the right, and v denotes the distance between the light source producing the flash and the optical center of the frontal camera in the z-direction. In addition or as an alternative thereto, the position of the corneal vertex in the y-direction proceeding from the reflection point is calculated by means of the correction calculation by adding $\Delta y = +/- r^* \sin \frac{1}{2}^*(\arctan l/(d-v))$, where r denotes an empirical value or an actual value for the corneal radius, d denotes the distance between the optical center of the frontal camera and the reflection point, v denotes the distance between the light source producing the flash and the optical center of the frontal camera in the z-direction and l denotes the distance between the light source and the optical center of the frontal camera in the y-direction, wherein the y-direction is orthogonal to the x-direction and to the z-direction and points upward in space.

The optical center is understood to be the projection center of the camera.

Here, the plus sign in the x-direction should be applied when the corneal vertex of the left eye from the view of the subject is detected; the minus sign should be applied to the right eye from the view of the subject. In the y-direction, the plus sign should be applied when the light source emitting the flash is positioned at a lower height than the frontal camera; the minus sign should be applied when it is assembled at a greater height.

The two correction formulae specified above emerge from the following considerations:

In order to determine the 3D coordinates of a point, it is necessary to detect the same point in at least two views, i.e., in a frontal image and a lateral image in this case. Since a vitreous humour of the eye is a type of sphere, it does not suffice to detect the reflection in two views. Firstly, the reflection is hardly visible or not at all visible in the lateral image on account of the large recording angle and, secondly, the reflection on the sphere migrates depending on the viewing direction of the camera; which would lead to very inaccurate 3D points.

Even without a reflection, a correction of the 3D position is necessary because the pupil lies slightly behind the vitreous humour surface and the camera view rays intersect slightly in front of the sphere as a result of the spherical form.

Typically, the pupil or the reflection point is detected by means of feature extraction and/or feature matching (feature comparison) and/or by means of machine learning by comparison with a plurality of data known in advance. This method step may be preceded by a face detection and/or a detection of facial features such as the eyes as a pre-processing step, in which there is a detection in respect of which image data belong to the face of the subject such that only these data are included in the detection. For further simplification of the method, provision can be made for a view ray of the frontal camera directed to the corneal vertex to be calculated from the frontal image and the view ray to be projected into the lateral image, and for the corneal vertex to be detected on the view ray that is projected into the lateral image.

In order to be able to undertake the determination of the corneal vertex in space for both eyes, it is typical to make provision of at least one calibrated third image or further lateral image that is recorded from a lateral position in respect of the head at the same time as the first image and the second image (frontal image and lateral image).

In principle, the at least one lateral image and, optionally, the at least one further lateral image may be recorded from recording directions that include only a small angle with the recording direction of the frontal image. However, an overlap between frontal and lateral images is not required in the method according to the disclosure. Regions of the images that possibly overlap are expediently not used for determining the corneal vertex. In this way, it is possible that the recording direction of the frontal image includes an angle of more than 60 to 120 degrees and, typically, of 90 degrees with the recording direction of the lateral image and, optionally, with the recording direction of the further lateral image.

Typically, the computer-implemented method according to the disclosure is carried out using an apparatus as described herein, for example in the following description of the figures.

The position of the corneal vertex in space, determined according to the disclosure, may typically be used for centering a spectacle lens in a spectacle frame and/or for grinding a spectacle lens into a spectacle frame. Here, in one method step and using the position of the at least one corneal vertex in space, at least one centration parameter is determined, in particular the vertex distance or, if both corneal vertices are available, the interpupillary distance, and, in a further method step, the at least one spectacle lens is centered in the spectacle frame using the centration parameter or parameters determined in the preceding method step or the at least one spectacle lens is ground into the spectacle frame on the basis of the centration parameter or parameters for an arrangement, determined in the preceding method step. In this way, it is possible to produce spectacle lenses and spectacles.

BRIEF DESCRIPTION OF THE DRAWINGS

The disclosure will now be described with reference to the drawings wherein:

FIG. 3A shows an illustration of the correction calculation in the case of a reflection-based determination of the position of the corneal vertex in the x-direction; and.

DESCRIPTION OF EXEMPLARY EMBODIMENTS

Figure 1A:
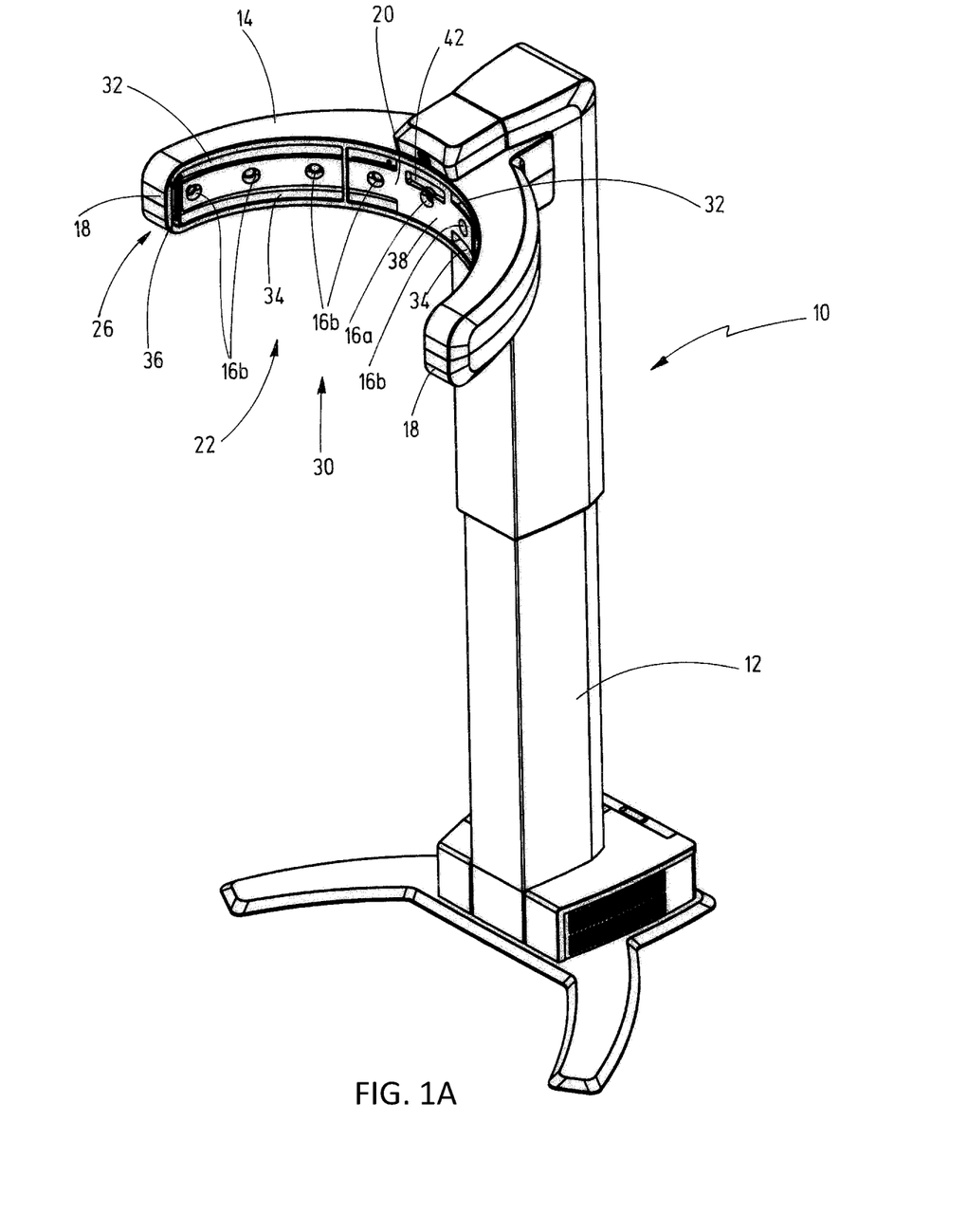
FIG. 1A shows an apparatus for determining centration parameters in a perspective view.
Figure 1B:
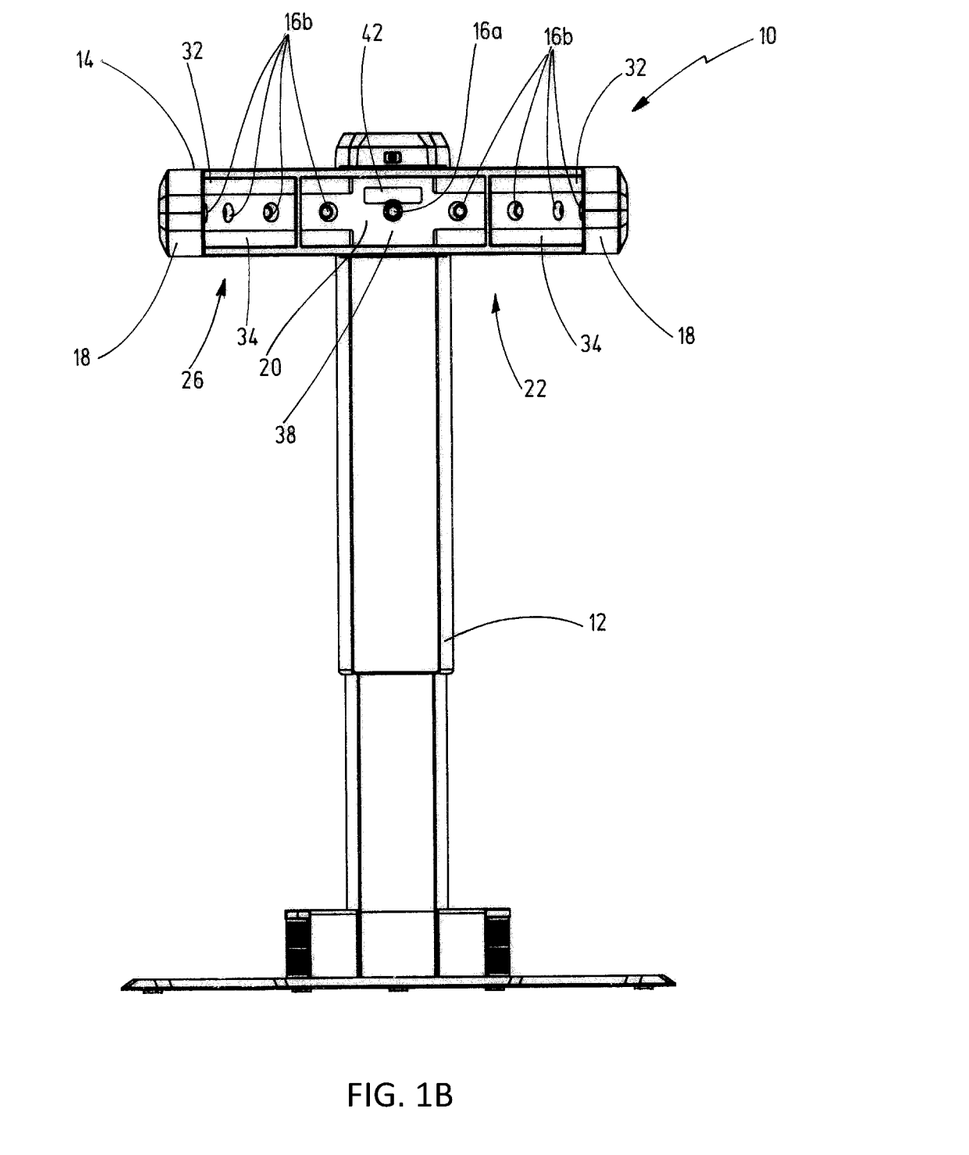
FIG. 1B shows an apparatus for determining centration parameters in a view from the front.

The apparatus 10 illustrated in FIGS. 1A and 1B serves to determine centration parameters for fitting spectacles. The apparatus has a column 12 which, in a height-adjustable manner, carries a camera carrier 14 which, in turn, carries a number of cameras 16a, 16b. In a plan view, the camera carrier 14 is bent into an approximately circular shape and extends between two free ends 18 which are arranged at a distance from one another. An inner face 20 of the camera carrier 14 encloses an interior 22, in which the head of a subject is situated when images are recorded by the cameras 16a, 16b, to the front, i.e., towards the column 12, and to the sides. In a direction extending between the free ends 18, the inner face 20 is bent in a concave manner and has, for example, the form of a portion of a lateral face of a cylinder, wherein a cylinder may have a circular or oval base. A lifting device, not illustrated in any more detail, is arranged in the column 12 in order to be able to position the camera carrier 14 at the correct height in relation to the head of the subject, it being possible to move the camera carrier 14 up-and-down in a motor-driven manner by way of the lifting device.

All cameras 16a, 16b are arranged in a camera arrangement 26 that extends between the free ends 18. In the present exemplary embodiment, the camera arrangement 26 is embodied as a camera row 26, the cameras 16a, 16b of which are all situated at the same height, with their optical axis being directed into the interior 22. In the present exemplary embodiment, the camera row 26 comprises a frontal camera 16a arranged in the center of the camera carrier 14, the optical axis of the frontal camera being directed frontally onto the face of the subject, and eight lateral cameras 16b that are arranged symmetrically in pairs in respect of a perpendicular plane of symmetry extending through the optical axis of the frontal camera 16a, four of the lateral cameras being directed onto the face of the subject from the left and four being directed onto the face of the subject from the right in each case. Moreover, the cameras 16a, 16b are calibrated in such a way that they are able to record calibrated images of the subject simultaneously. The calibration comprises the extrinsic properties, such as the relative alignment of the optical axes and the relative arrangement with respect to one another in space, and their intrinsic properties, i.e., the properties of the cameras themselves, which define how a point in space, which is situated in the internal coordinate system of the respective camera, is mapped onto the coordinates of the pixels of the recorded image.

The camera carrier 14 only encloses the interior 22 to the front, towards the column 12, and to the sides, i.e., to the left and right of the head of the subject. Toward the top, the bottom and toward a rear side 30, the interior is open, wherein the free ends 18 have a distance from one another of at least 25 cm, such that the subject can comfortably approach from the rear side. The distance is 70 to 80 cm in the shown exemplary embodiment.

In order to illuminate the interior 22, provision is made of an illumination device having an upper light strip 32 extending above the camera row 26 and a lower light strip 34 extending below the camera row 26, the light strips having a plurality of LEDs as lighting means in each case. The upper light strip 32 and the lower light strip 34 each extend, continuously or with interruptions, over a length which is at least as long at the length of the camera row 26 as measured in the circumferential direction between the free ends 18. This corresponds to a circumferential angle of at least 160 degrees. Near the free ends 18, the upper light strip 32 and the lower light strip 34 are connected to one another, in each case by means of a further light strip 36 that extends in the vertical direction. Consequently, the camera row 26 is framed in the entirety thereof by at least one row of LEDs. The apparatus 10 moreover has an open-loop or closed-loop control device, not illustrated in any more detail in the figures, by means of which the light intensity emitted by the LEDs can be controlled or regulated depending on the light intensity detected by the cameras 16a, 16b. Here, the LEDs of the light strips 32, 34, 36 are combined into sectors, the emitted light intensities of which can be controlled or regulated separately from one another. Moreover, provision is made for the light intensities emitted by the individual LEDs also to be able to be controlled or regulated separately from one another by means of the open-loop or closed-loop control device.

In order to be able to correctly position the subject in the interior 22, the two lateral cameras 16b closest to the frontal camera 16a are configured to measure the distance of the head of the subject from the center 38 of the camera carrier 14. The subject is shown whether or not they are standing correctly by means of a display unit, which is not displayed in any more detail. The display unit has a plurality of differently colored light sources arranged in a row. The central light source lights up green when the subject stands correctly. Proceeding from the central light source, there is, in this sequence, a green, an orange, and a red light source in each direction, the light sources indicating, in accordance with their color, if the subject is slightly, clearly, or much too far away from the center 38 of the camera carrier 14 or if the subject stands slightly, clearly, or much too close to the center 38. In order to ensure that the viewing direction of the subject is directed to infinity when determining the centration parameters, a fixation device 42 arranged at the camera carrier 14 is provided, the fixation device producing a fixation pattern in the form of a speckle pattern for the subject. The fixation pattern is arranged slightly higher than the frontal camera 16a so that the subject peers over the latter. In this way, the subject's face can be recorded to the greatest possible extent.

The apparatus 10 is also suited, in particular, to produce an avatar of the head of the subject, which may be used for determining the centration parameters. To this end, calibrated images of the head of the subject without spectacles or spectacle frame are recorded by the cameras 16a, 16b. A depth profile of the head, which images the latter very well as an approximation, is created by means of a suitable process for geometric position determination, such as triangulation. The head is imaged by a plurality of points which can be connected to one another by a mesh pattern or else be stored as a point cloud. In the subsequent determination of the centration parameters, the avatar thus ascertained may be used to determine centration parameters which cannot be determined, or can only be determined approximately, on account of the geometric properties of the spectacles or the spectacle frame worn by the subject. By way of example, a wide frame side may cover the eye in a lateral recording to such an extent that the vertex distance cannot be determined or can only be determined very inaccurately. Moreover, tinted or strongly reflecting spectacles may not allow the eyes to be identified, or only be identified very badly. In order to counteract this, the depth profile of the avatar is projected onto the images, recorded by the cameras 16a, 16b, of the subject wearing the spectacles or spectacle frame and the centration parameters, which can only be determined very unsatisfactorily on account of the sight being restricted by the spectacles or spectacle frame, are determined from the image data of the avatar. Here, for the purposes of minimizing deviations, the avatar may be fitted to the images of the subject wearing the spectacles or spectacle frame.

The above-described apparatus 10 can be used as follows for both a pupil-based detection of a corneal vertex and for a reflection-based detection of a corneal vertex in both eyes of the subject.

Figure 2:
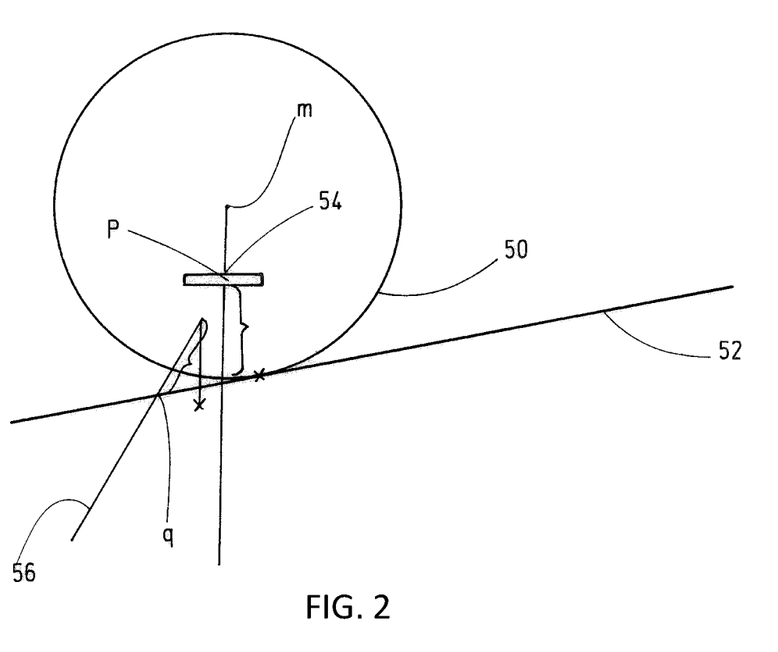
FIG. 2 shows an illustration of the correction calculation in the case of a pupil-based determination of the position of the corneal vertex.

In the pupil-based method according to FIG. 2, the position of the corneal vertex in space is initially determined to a first approximation as the point of intersection q of a first view ray 52, tangential to the cornea 50, from one of the lateral cameras 16b recording a lateral image of the subject with a second view ray 56, directed onto the pupil 54, from a frontal camera 16a recording a frontal image of the subject. A corrected position of the corneal vertex in space is calculated by a correction calculation using the equation $a=q+\mu^*v+\mu^*w$. Here, $\mu$ is an empirical value or an actual value for the distance between the pupil center and the corneal vertex, which typically assumes values between 2.5 mm and 4 mm. v is a unit vector in the spatial direction from the pupil center p to the frontal camera 16a, the coordinates of which are specified using the variable c1, and it is calculated as $v=(p-c1)/|p-c1|$. w is a unit vector of the viewing direction extending through the center m of the corneal sphere, the viewing direction being directed onto the fixation pattern of the fixation device 42 at the spatial point t, and it is calculated as $w=(t-m)/|t-m|$. All values a, q, p, c1, t and m are three-dimensional vectors.

Figure 3A:
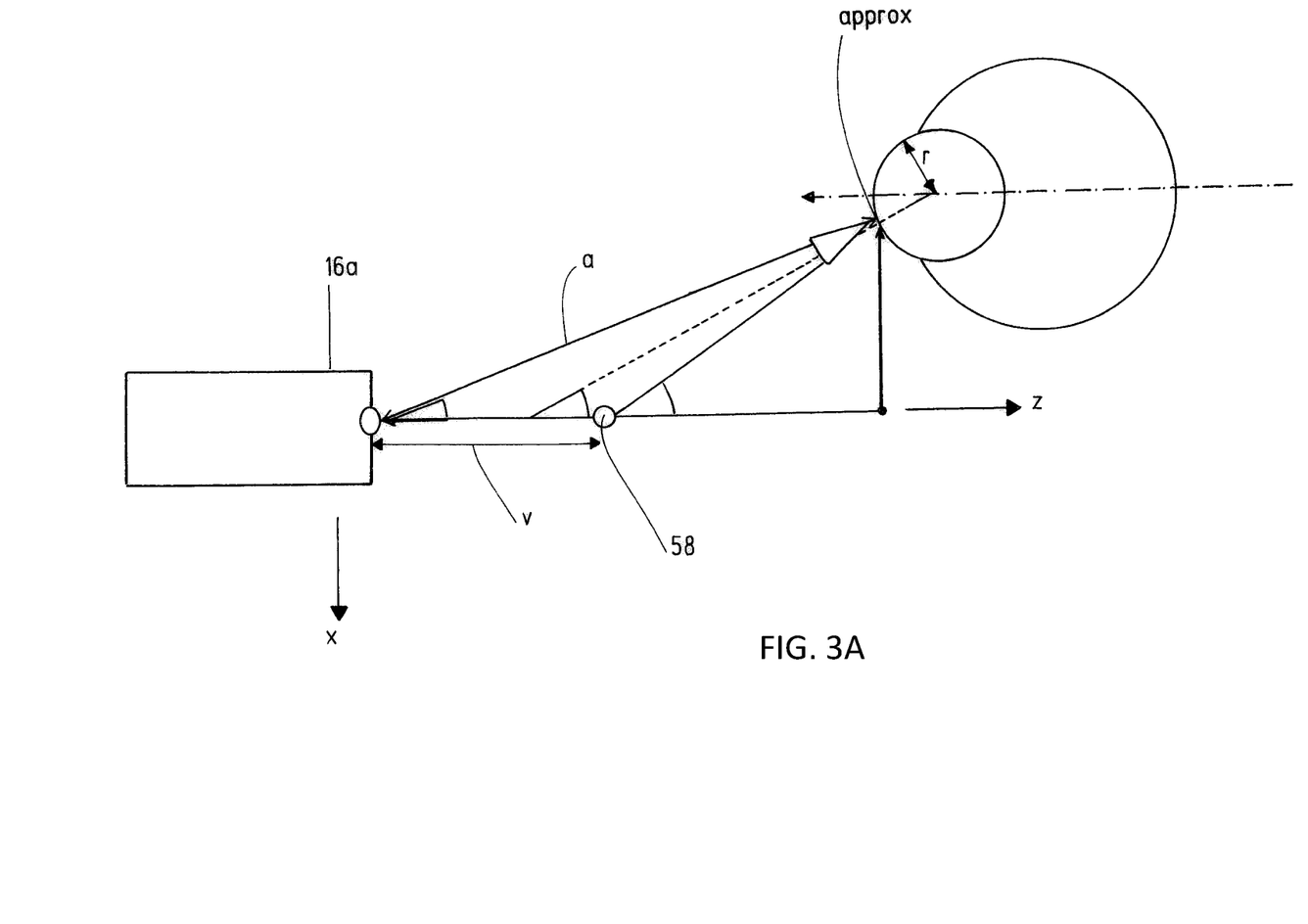
Figure 3B:
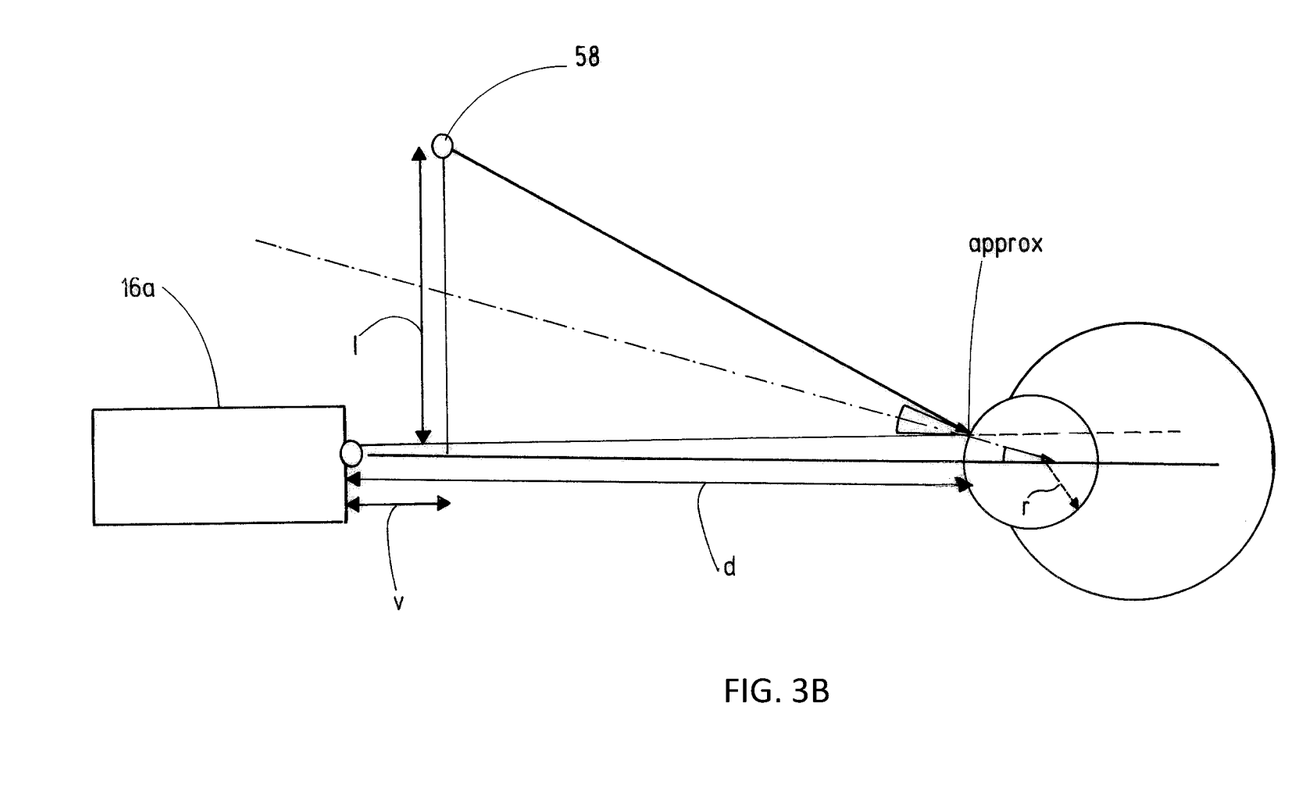
FIG. 3B shows an illustration of the correction calculation in the case of a reflection-based determination of the position of the corneal vertex in the y-direction.

Two correction calculations have to be undertaken in the reflection-based determination of the position of the corneal vertex according to FIGS. 3A and 3B, wherein the first correction calculation (FIG. 3A) relates to a correction in the x-direction and the second correction (FIG. 3B) relates to a correction in the y-direction. These spatial directions are set by an internal coordinate system of the frontal camera 16a, which has its origin in the optical center of the frontal camera 16a. Here, the z-direction is set by the viewing direction of the frontal camera 16a, the x-direction is a direction which extends horizontally and orthogonally with respect to the z-direction and which points to the right when observed in the direction of the latter, and the y-direction extends orthogonally to the x-direction and to the z-direction and points upward in space. In the case of the reflection-based measurement, a flash is emitted by a light source, an LED 58 in the present case, the reflection of the flash on the cornea being detected by the frontal camera 16a and at least one of the lateral cameras 16b and forming the first approximation for the position of the corneal vertex in space. In FIGS. 3A and 3B, the reflection point is denoted "approx." In the x-direction, a correction is undertaken by adding $\Delta x=+/-r^*\sin(\frac{1}{2}^*(\arccos z/a+\arctan x/(z-v)))$ to the x-coordinate of the reflection point approx, wherein the plus sign should be used in an application to the left eye and the minus sign should be used in an application to the right eye (cf. FIG. 3A). Here, r is an empirical value or an actual value for the corneal radius, which is typically approximately 8 mm. a is the distance of the optical center of the frontal camera 16a from the reflection point approx and v is the distance of the LED 58 from the optical center of the frontal camera 16a in the z-direction. Once again, x and z are the coordinates in the x- and z-directions.

In the y-direction, a correction is undertaken by adding $\Delta y=+/-r^*\sin\frac{1}{2}^*(\arctan l/(d-v))$, proceeding from the reflection point approx. Once again, r is the empirical value or an actual value for the corneal radius, d is the distance of the optical center of the frontal camera 16a from the reflection point approx in the z-direction, v is the distance of the LED 58 from the optical center of the frontal camera 16a in the z-direction and l is the distance of the LED 58 from the optical center of the frontal camera 16a in the y-direction.

The plus sign is used when the LED 58 is arranged below the frontal camera 16a, i.e., if the y-coordinate of the LED 58 is smaller than the y-coordinate of the frontal camera 16a or of the optical center of the latter. The minus sign is used if the LED is arranged above the frontal camera 16a.

In the above-described method, the pupil or the reflection point approx can be detected, for example, by means of feature extraction and/or feature matching and/or by means of machine learning by comparison with a plurality of data known in advance. This detection step can be preceded by a step in which a face detector identifies which pixels belong to the face of the subject or to the subject's eye area, such that there can already be a restricted search for the pupil or the reflection point approx.

Exemplary embodiments of the disclosure are reproduced in the following numerals:

1. Computer-implemented method for detecting a corneal vertex, wherein a frontal image of a head and a lateral image of the head are provided, the images being calibrated to one another, wherein the position of the corneal vertex in space is determined from the frontal image and the lateral image by means of a geometric position determination.

2. Computer-implemented method according to numeral 1, characterized in that a triangulation method is used in the geometric position determination.

3. Computer-implemented method according to numeral 1 or 2, characterized in that the position of the corneal vertex is subjected to a correction calculation.

4. Computer-implemented method according to any one of the preceding numerals, characterized in that the position of the corneal vertex in space is determined to a first approximation as the point of intersection q of a first view ray (52), tangential to the cornea (50), from a lateral camera (16b) recording the lateral image with a second view ray (56), directed onto the pupil (54), from a frontal camera (16a) recording the frontal image.

5. Computer-implemented method according to numeral 3 and numeral 4, characterized in that the position of the corneal vertex is calculated according to $a=q+\mu^*v+\mu^*w$ by means of the correction calculation, where a denotes the position vector of the corneal vertex in space after carrying out the correction calculation, q denotes the position of the corneal vertex to a first approximation, $\mu$ denotes an empirical value or an actual value for the distance between a pupil center and the corneal vertex, v denotes a unit vector in the spatial direction from the pupil center to the frontal camera and w denotes a unit vector in the viewing direction extending through the center of a corneal sphere.

6. Computer-implemented method according to any one of numerals 1 to 3, characterized in that a flash is produced when recording the images and in that the position of the corneal vertex in space is determined to a first approximation as the position of the reflection point of the flash on the cornea.

7. Computer-implemented method according to numeral 3 and according to numeral 6, characterized in that the position of the corneal vertex in the horizontal direction proceeding from the reflection point is calculated with the correction calculation by adding $\Delta x=+/-r^*\sin(\frac{1}{2}^*(\arccos z/a+\arctan x/(z-v)))$ to the x-coordinate, where r denotes an empirical value or an actual value for the corneal radius, a denotes the distance between the optical center of a frontal camera (16a) recording the frontal image and the reflection point, x and z denote the x- and z-coordinates of the reflection point in a coordinate system with the origin in the optical center of the frontal camera (16a), wherein the viewing direction of the frontal camera corresponds to the z-direction and the x-direction is horizontally orthogonal to the z-direction and, when observed in the z-direction, points to the right, and v denotes the distance between the light source (58) producing the flash and the optical center of the frontal camera (16*a*) in the z-direction.

Computer-implemented method according to numeral 3 and according to numeral 6 or 7, characterized in that the position of the corneal vertex in the y-direction proceeding from the reflection point is calculated by means of the correction calculation by adding $\Delta y = +/- r^* \sin \frac{1}{2}^*(\arctan l/(d-v))$, where r denotes an empirical value or an actual value for the corneal radius, d denotes the distance between the optical center of the frontal camera (16*a*) and the reflection point in the z-direction, v denotes the distance between the light source (58) producing the flash and the optical center of the frontal camera (16*a*) in the z-direction and l denotes the distance between the light source (58) and the optical center of the frontal camera (16*a*) in the y-direction, wherein the y-direction is orthogonal to the x-direction and to the z-direction and points upward in space.

9. Computer-implemented method according to any one of numerals 4 to 8, characterized in that the pupil or the reflection point is detected by means of feature extraction and/or feature matching and/or by means of machine learning by comparison with a plurality of data known in advance.

10. Computer-implemented method according to any one of the preceding numerals, characterized in that a view ray of the frontal camera (16*a*) directed to the corneal vertex is calculated from the frontal image and the view ray is projected into the lateral image, and in that the corneal vertex is detected on the view ray that is projected into the lateral image.

11. Computer-implemented method according to any one of the preceding numerals, characterized in that provision is made of at least one calibrated third image that is recorded from a lateral position in respect of the head at the same time as the first image and the second image.

12. Computer-implemented method according to any one of the preceding numerals, characterized in that the recording direction of the frontal image includes an angle of more than 60 to 120 degrees and, preferably, of 90 degrees with the recording direction of the lateral image and, optionally, with the recording direction of the further lateral image.

13. Use of a computer-implemented method according to any one of the preceding numerals for determining centration parameters, in particular for determining the vertex distance of a spectacle frame or a spectacles-wearing subject.

14. Computer program with program code for carrying out all of the method steps according to any one of numerals 1 to 12, when the computer program is loaded onto a computer and/or executed on a computer.

15. Use of an apparatus (10) for carrying out a computer-implemented method according to any one of numerals 1 to 12, wherein the apparatus (10) has a camera carrier (14), which partly encloses an interior (22) that is open to the top, to the bottom and to a rear side (30) and which carries at least three cameras (16*a*, 16*b*) which are arranged between two free ends (18) of the camera carrier (14) and directed onto the interior (22), wherein the camera carrier (14) has an illumination device (32, 34, 36) for illuminating the interior (22).

16. Computer, comprising a memory, wherein the computer program according to numeral 14 is stored in the memory, and a processor for executing the computer program stored in the memory.

17. Computer according to numeral 16, characterized in that the processor is configured to provide a frontal image of a head and a lateral image of the head, the images being calibrated to one another, and to determine the position of the corneal vertex in space from the frontal image and the lateral image by means of a geometric position determination.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer-implemented method for detecting a position of a corneal vertex, the method comprising:
   recording a frontal image of a head and a lateral image of the head,
   calibrating the frontal image and the lateral image to one another,
   determining a position of a corneal vertex in space from the frontal image and the lateral image with a geometric position determination, the geometric position determination including:
      determining a position of the corneal vertex in space to a first approximation as the point of intersection q of:
         a first view ray, tangential to the cornea, from a lateral camera recording the lateral image, with
         a second view ray, directed onto the pupil, from a frontal camera recording the frontal image,
   detecting at least one of a position of a pupil or detecting a position of a reflection point of a flash,
   producing the flash when recording the frontal image and the lateral image and the position of the corneal vertex in space is determined to the first approximation as a position of the reflection point of the flash on the cornea, and
   detecting the position of the pupil or detecting the position of the reflection point by performing at least one of:
      extracting a feature, matching a feature, or comparing by machine learning a plurality of data known in advance.

2. The computer-implemented method according to claim 1, further comprising:
   selecting the frontal image and the lateral image to not overlap or selecting only mutually non-overlapping regions of the frontal image and the lateral image to detect the position of the corneal vertex.

3. A computer-implemented method for detecting a position of a corneal vertex, the method comprising:
   recording a frontal image of a head and a lateral image of the head,
   calibrating the frontal image and the lateral image to one another, and
   determining a position of a corneal vertex in space from the frontal image and the lateral image with a geometric position determination, the geometric position determination including:
   selecting the frontal image and the lateral image to not overlap or selecting only mutually non-overlapping regions of the frontal image and the lateral image to detect the position of the corneal vertex.

4. The computer-implemented method according to claim 1, wherein a view ray of the frontal camera directed to the corneal vertex is calculated from the frontal image and the view ray is projected into the lateral image, and wherein the position of the corneal vertex is detected on the view ray that is projected into the lateral image.

5. A computer-implemented method for detecting a position of a corneal vertex, the method comprising:
recording a frontal image of a head and a lateral image of the head,
calibrating the frontal image and the lateral image to one another, and
determining a position of a corneal vertex in space from the frontal image and the lateral image with a geometric position determination, wherein a view ray of the frontal camera directed to the corneal vertex is calculated from the frontal image and the view ray is projected into the lateral image, and wherein the position of the corneal vertex is detected on the view ray that is projected into the lateral image.

6. The computer-implemented method according to claim 1, wherein the geometric position determination includes a triangulation method.

7. The computer-implemented method according to claim 1, further comprising:
performing a correction calculation of the position of the corneal vertex.

8. The computer-implemented method according to claim 3, further comprising:
determining a position of the corneal vertex in space to a first approximation as the point of intersection q of:
a first view ray, tangential to the cornea, from a lateral camera recording the lateral image, with
a second view ray, directed onto the pupil, from a frontal camera recording the frontal image.

9. The computer-implemented method according to claim 7, wherein the correction calculation comprises:
calculating the position of the corneal vertex according to $a = q + \mu^* v + \mu^* w$, wherein a denotes the position vector of the corneal vertex in space after carrying out the correction calculation, q denotes the position of the corneal vertex to a first approximation, $\mu$ denotes an empirical value or an actual value for the distance between a pupil center and the corneal vertex, v denotes a unit vector in the spatial direction from the pupil center to the frontal camera and w denotes a unit vector in the viewing direction extending through the center of a corneal sphere.

10. The computer-implemented method according to claim 1, wherein the flash is produced when recording the images, and wherein the position of the corneal vertex in space is determined to a first approximation as the position of the reflection point of the flash on the cornea.

11. The computer-implemented method according to claim 7, wherein the correction calculation comprises:
calculating the position of the corneal vertex in the horizontal direction proceeding from the reflection point by adding $\Delta x = +/- r^* \sin(\frac{1}{2}^*(\arccos z/a + \arctan x/(z-v)))$ to the x-coordinate, wherein r denotes an empirical value or an actual value for the corneal radius, a denotes the distance between the optical center of the frontal camera recording the frontal image and the reflection point, x and z denote the x- and z-coordinates of the reflection point in a coordinate system with the origin at the optical center of the frontal camera, wherein the viewing direction of the frontal camera corresponds to the z-direction and the x-direction is horizontally orthogonal to the z-direction and, when observed in the z-direction, points to the right, and v denotes the distance between the light source producing the flash and the optical center of the frontal camera in the z-direction.

12. The computer-implemented method according to claim 7, wherein the correction calculation comprises:
calculating the position of the corneal vertex in the y-direction proceeding from the reflection point by adding $\Delta y = +/- r^* \sin \frac{1}{2}^*(\arctan l/(d-v))$, wherein r denotes an empirical value or an actual value for the corneal radius, d denotes the distance between the optical center of the frontal camera and the reflection point in the z-direction, v denotes the distance between the light source producing the flash and the optical center of the frontal camera in the z-direction and l denotes the distance between the light source and the optical center of the frontal camera in the y-direction, wherein the y-direction is orthogonal to the x-direction and to the z-direction and points upward in space.

13. A computer-implemented method for detecting a position of a corneal vertex, the method comprising:
recording a frontal image of a head and a lateral image of the head,
calibrating the frontal image and the lateral image to one another,
determining a position of a corneal vertex in space from the frontal image and the lateral image with a geometric position determination, the geometric position determination including:
determining a position of the corneal vertex in space to a first approximation as the point of intersection q of:
a first view ray, tangential to the cornea, from a lateral camera recording the lateral image, with
a second view ray, directed onto the pupil, from a frontal camera recording the frontal image, and
calculating the position of the corneal vertex according to $a = q + \mu^* v + \mu^* w$, wherein a denotes the position vector of the corneal vertex in space after carrying out the correction calculation, q denotes the position of the corneal vertex to a first approximation, $\mu$ denotes an empirical value or an actual value for the distance between a pupil center and the corneal vertex, v denotes a unit vector in the spatial direction from the pupil center to the frontal camera and w denotes a unit vector in the viewing direction extending through the center of a corneal sphere.

14. A computer-implemented method for detecting a position of a corneal vertex, the method comprising:
recording a frontal image of a head and a lateral image of the head,
calibrating the frontal image and the lateral image to one another,
determining a position of a corneal vertex in space from the frontal image and the lateral image with a geometric position determination, the geometric position determination including:
performing a correction calculation of the position of the corneal vertex,
detecting a position of a reflection point of a flash,
producing the flash when recording the frontal image and the lateral image and the position of the corneal vertex in space is determined to the first approximation as a position of the reflection point of the flash on the cornea, and performing at least one of:

calculating the position of the corneal vertex in the horizontal direction proceeding from the reflection point by adding $\Delta x=+/-r*\sin(\frac{1}{2}*(\arccos z/a+\arctan x/(z-v)))$ to the x-coordinate, wherein r denotes an empirical value or an actual value for the corneal radius, a denotes the distance between the optical center of the frontal camera recording the frontal image and the reflection point, x and z denote the x- and z-coordinates of the reflection point in a coordinate system with the origin at the optical center of the frontal camera, wherein the viewing direction of the frontal camera corresponds to the z-direction and the x-direction is horizontally orthogonal to the z-direction and, when observed in the z-direction, points to the right, and v denotes the distance between the light source producing the flash and the optical center of the frontal camera in the z-direction; or calculating the position of the corneal vertex in the y-direction proceeding from the reflection point by adding $\Delta y=+/-r*\sin \frac{1}{2}*(\arctan l/(d-v))$, wherein r denotes an empirical value or an actual value for the corneal radius, d denotes the distance between the optical center of the frontal camera and the reflection point in the z-direction, v denotes the distance between the light source producing the flash and the optical center of the frontal camera in the z-direction and l denotes the distance between the light source and the optical center of the frontal camera in the y-direction, wherein the y-direction is orthogonal to the x-direction and to the z-direction and points upward in space.

15. The computer-implemented method according to claim 3, further comprising:
extracting a feature, matching a feature, or comparing by machine learning a plurality of data known in advance.

16. The computer-implemented method according to claim 1, wherein a view ray of the frontal camera directed to the corneal vertex is calculated from the frontal image and the view ray is projected into the lateral image, and wherein the position of the corneal vertex is detected on the view ray that is projected into the lateral image.

17. The computer-implemented method according to claim 1, further comprising:
recording at least one further calibrated lateral image from a lateral position in respect of the head at the same time as the frontal image and the lateral image.

18. The computer-implemented method according to claim 4, further comprising:
selecting the frontal image and the lateral image to not overlap or selecting only mutually non-overlapping regions of the frontal image and the lateral image to detect the position of the corneal vertex.

19. The computer-implemented method according to claim 1, wherein a recording direction of the frontal image includes an angle of more than 60 and up to 120 degrees with the recording direction of the lateral image and, optionally, with the recording direction of the further lateral image.

20. The computer-implemented method according to claim 1, wherein the position of the corneal vertex is determined to calculate a vertex distance of a spectacle frame or a spectacles-wearing subject.

21. A computer program with program code for carrying out the method steps according to claim 1 when the computer program is loaded onto a computer and/or executed on a computer.

22. An apparatus for carrying out the computer-implemented method according to claim 1, the apparatus comprising:
a camera carrier, which partly encloses an interior that is open to a top, to a bottom and to a rear side, the camera carrier including:
at least three cameras, which are arranged between two free ends of the camera carrier and directed onto the interior, and
an illumination device for illuminating the interior.

23. A computer, comprising a memory, wherein the computer program according to claim 21 is stored in the memory, and a processor for executing the computer program stored in the memory.

24. The computer according to claim 23, wherein the processor is configured to provide a frontal image of a head and a lateral image of the head, the images being calibrated to one another, and to determine the position of the corneal vertex in space from the frontal image and the lateral image by means of a geometric position determination.

25. An apparatus for detecting a position of a corneal vertex comprising:
a frontal camera for recording a frontal image,
a lateral camera for recording a lateral image, and
a computer, which has a memory in which the computer program according to claim 21 is stored, and the computer having a processor configured to execute the computer program stored in the memory.

26. A method for centering at least one spectacle lens in a spectacle frame, wherein, in a first method step, the position of at least one corneal vertex in space is detected using the method according to claim 1,
wherein, in a second method step, at least one centration parameter is determined using the position of the at least one corneal vertex in space, and
wherein, in a third method step, the at least one spectacle lens is centered in the spectacle frame using the centration parameter or parameters determined in the second method step.

27. A method for grinding at least one spectacle lens into a spectacle frame, wherein, in a first method step, the position of at least one corneal vertex in space is detected using the method according to claim 1,
wherein, in a second method step, at least one centration parameter is determined using the position of the at least one corneal vertex in space, and
wherein, in a third method step, the at least one spectacle lens is ground in the spectacle frame on the basis of the centration parameter or parameters determined in the second method step for an arrangement.

28. A method for producing a spectacle lens, comprising:
grinding at least one spectacle lens into a spectacle frame according to claim 27.

29. A method for producing spectacles, comprising:
grinding at least one spectacle lens into a spectacle frame according to claim 27.

* * * * *